United States Patent [19]
Kroll et al.

[11] Patent Number: 5,351,687
[45] Date of Patent: Oct. 4, 1994

[54] METHOD AND APPARATUS FOR NON-INVASIVELY DETERMINING A PATIENT'S SUSCEPTIBILITY TO VENTRICULAR ARRHYTHMIAS

[76] Inventors: Mark W. Kroll, 13011 Brenwood Trail, Minnetonka, Minn. 55343; Karl J. F. Kroll, 550 W. Sandhurst #125, Roseville, Minn. 55113

[21] Appl. No.: 890,957

[22] Filed: May 29, 1992

Related U.S. Application Data

[62] Division of Ser. No. 563,106, Aug. 6, 1990, Pat. No. 5,117,834.

[51] Int. Cl.$^5$ ............................. A61B 5/05
[52] U.S. Cl. ............................. 128/653.1
[58] Field of Search .......... 128/419 PT, 696, 697, 128/653.1, 653.5, 702, 705; 607/27

[56] References Cited

U.S. PATENT DOCUMENTS

| | | | |
|---|---|---|---|
| 4,279,257 | 7/1981 | Hochstein | 128/653.1 |
| 4,324,255 | 4/1982 | Barach et al. | 128/653.1 |
| 4,793,355 | 12/1988 | Crum et al. | 128/653.1 |
| 4,801,882 | 1/1989 | Daalmans | 128/653.1 |
| 4,892,104 | 1/1990 | Ito et al. | 128/419 PT |

Primary Examiner—William E. Kamm
Attorney, Agent, or Firm—Patterson & Keough

[57] ABSTRACT

A method and device for noninvasively determining a patient's susceptibility to ventricular arrhythmias is presented. The method is comprised of the steps of injecting small and safe amounts of electromagnetic energy into a patient and observing possible effects on the electrocardiogram or magnetocardiogram. The device is comprised of a means to inject small and safe amounts of electromagnetic energy into a patient, electrocardiogram or magnetocardiogram sensors connected to the patient, and means to display the signals of the electrocardiogram or magnetocardiogram sensors.

2 Claims, 18 Drawing Sheets

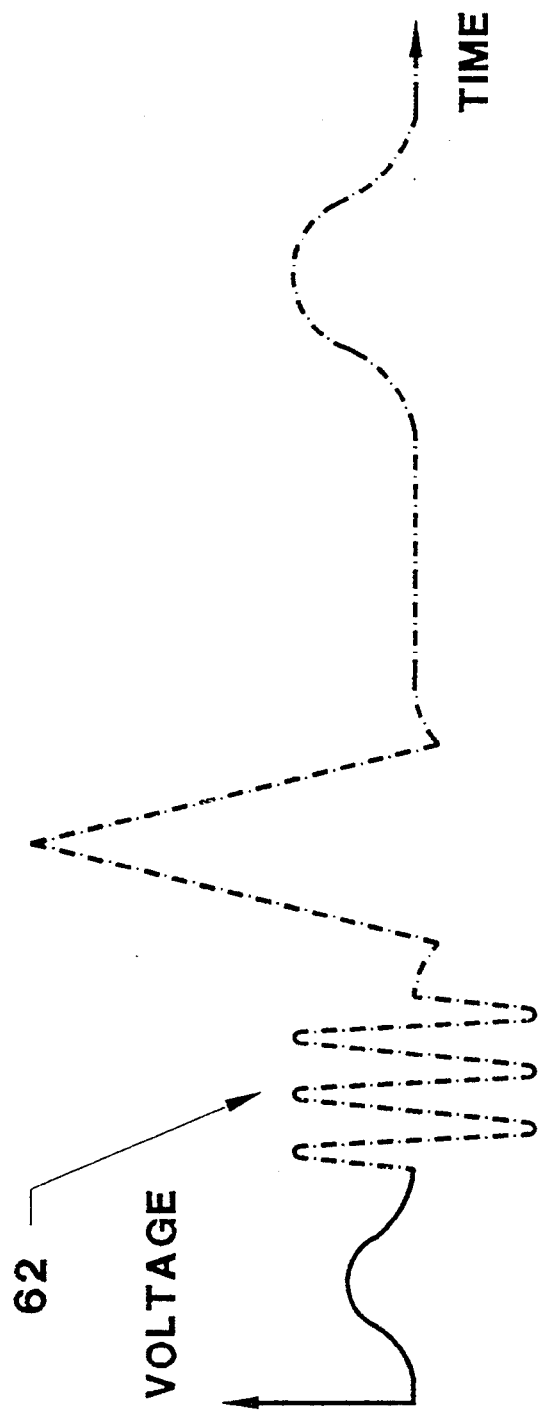

METHOD AND APPARATUS FOR NON-INVASIVELY DETERMINING A PATIENT'S SUSCEPTIBILITY TO VENTRICULAR ARRHYTHMIAS

This patent application is a division of U.S. Ser. No. 07/563,106, filed Aug. 6, 1990, entitled "Method and Apparatus for Non-invasively Determining a Patient's Susceptibility to Ventricular Arrhythmias", now U.S. Pat. No. 5,117,834, issuing Jun. 2, 1992, to the same applicant.

BACKGROUND OF THE INVENTION

Many individuals die every year from "cardiac electrical death." The typical sequence is that the person has a congenital electrical problem or underlying organic heart disease for years. This can suddenly cause the the lower part of the heart ("ventricles") to race out of control (ventricular "tachycardia") with an inefficient excessive rate. The ventricular tachycardia can then rapidly deteriorate into an electrical storm (ventricular "fibrillation") in which there is no pumping action. Unconsciousness occurs within 30 seconds and death follows in minutes.

There are three main therapies for such patients. The first therapy is antiarrhythmic drugs. Unfortunately, these have many side effects. The second therapy is the implantation of a defibrillator. The implantable defibrillator is designed to sense the ventricular tachycardia or ventricular fibrillation and deliver appropriate pacing pulses or a high energy defibrillation shock to the heart to restore normal ("sinus") rhythm. The third therapy is "ablation" in which the unstable heart cells, responsible for the arrhythmia, are destroyed through freezing or burning.

Because of the side effects of the drugs and the surgical risks involved with the implantable defibrillator or ablation therapy, patients are examined very carefully before receiving their therapies. Their propensity for ventricular tachycardia or ventricular fibrillation is determined by attempting to "induce" one of these conditions. A current carrying catheter is introduced through the leg and one end is moved about in the ventricle. Electrical pulses are then introduced into the ventricle in an attempt to destabilize the heart. If either a ventricular tachycardia or a ventricular fibrillation (collectively referred to as a ventricular arrhythmia) occurs, the patient is said to be "inducible" and the appropriate therapies are then prescribed.

The inducibility study is also referred to as an electrophysiological study or a PVS (programmed ventricular stimulation) study. While the inducibility study allows lifesaving therapies, it also has pain and risks of death associated with it. Hence there is a need for a noninvasive and safe means of predicting inducibility.

SUMMARY OF THE INVENTION

Accordingly, the present invention provides a noninvasive and safe method and device to predict inducibility.

It is known that passing very large direct current ("DC") continuous or DC pulsed currents through the patient's chest ("transthoracic" currents), on the order of 1 to 10 Amps can cause fibrillation. Smaller transthoracic pulsed currents, on the order of 100 mA, can pace the heart (control or "capture" the heart to the rate of the external pulses).

Still smaller transthoracic currents, on the order of 10 mA, will not typically interfere with the heart rhythm. A current of 1 mA alternating current (AC) is about the threshold of perception for the typical individual. Currents of 10 $\mu$A to 100 $\mu$A AC (depending on the organization) are considered totally safe to the human body for medical monitors by various standards and safety organizations. AC is much more dangerous to the heart than is DC. For example, Underwriters Laboratory allows electric fence currents of 5 mA (pulsed DC) but appliances are limited to a leakage current of 500 $\mu$A (60 Hz AC).

Patients that are inducible tend to have some heart ("myocardial") cells that are significantly less stable than normal. These cells are usually very close to firing (triggering or "depolarizing") and may fire under stressful conditions or even at random. That is the primary reason why they can start a ventricular tachycardia and ventricular fibrillation and why the patient is inducible. A section of unstable cells causing ventricular arrhythmias is referred to as an "ectopic focus."

A section of heart cells can also cause ventricular arrhythmias by offering very slow passage of the pulse wave through their section. This slow passage can cause delays and inappropriate feedback which may result in a ventricular arrhythmia. This circular oscillation is referred to as a "reentrant" ventricular arrhythmia. Fortunately, the conditions that lead to cells being slow and allowing reentry also tend; to make the cells unstable. Thus one primarily needs to test for instability to correctly predict inducibility.

Very small amounts of current through the heart may be sufficient to cause these "unstable" cells to depolarize, i.e. fire. By passing small and safe amounts of electromagnetic energy through the patient's heart and noting small changes in the electrocardiogram (EKG) or magnetocardiogram (MKG) it is possible to noninvasively detect these unstable cells that could cause life threatening ventricular arrhythmias.

The heart can be stimulated and the heartbeat detected both by magnetic and electric techniques. The electrical techniques will be discussed in detail here. The adaptation to magnetic techniques will be obvious to those skilled in the art.

For maximum safety, this "microinduction" method and device begins with extremely small current pulses such as 100 $\mu$A with a duration of 250 $\mu$sec. These currents and duration may then be slowly increased with continuous monitoring of EKG changes. If significant EKG changes are detected, the test is terminated and end state results reported. If not, the pulse currents and/or durations are gradually increased until either changes are noted or a maximum safe level of stimulation is achieved.

For additional safety, the microinduction pulses are initially positioned in the safest part of the cardiac cycle, the "PR" segment.

Other objects, advantages, and novel features of the present invention will be apparent from the following detailed description when read in view of the appended claims and attached drawings.

BRIEF DESCRIPTION OF THE DRAWINGS

FIG. 17 shows an alternative embodiment of the invention using a burst of high frequency stimulation.

DESCRIPTION OF THE PREFERRED EMBODIMENT

Figure 1:
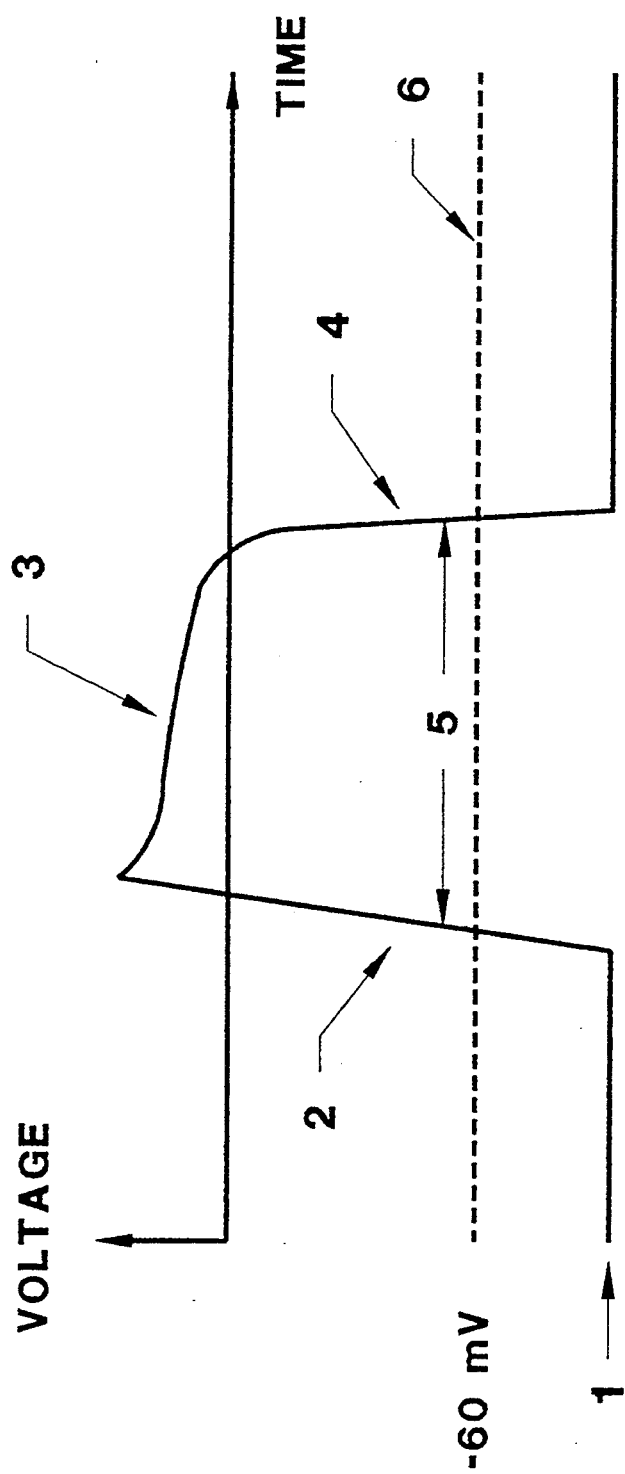
FIG. 1 is the transmembrane action potential of a healthy heart cell.

The method of this invention can be understood by referring to FIG. 1 which shows a normal transmembrane action potential or simply "action potential." This is the voltage ("potential") difference between the inside and outside (hence "transmembrane") of an individual heart cell when it fires or triggers (hence "action"). The lower line 1 shows the "resting potential" or voltage that the cell assumes between firings. It is also referred to as the "polarized" or "repolarized" voltage. A typical value is −85 mV. The rising line 2 represents the first stage ("onset") of the firing of the cell. A typical value for the slope is 300 V/S. The peak voltage attained is about 25 mV. There is a plateau region of mostly positive voltage 3 and a return (to resting) process of the cell (repolarization) 4. The total time that the cell is fired is called the potential duration time 5.

The cell has a firing threshold level 6 of approximately −60 mV. When this voltage is achieved, due to a combination of internal or external (mostly external) processes, the cell proceeds inexorably towards and through a complete firing cycle.

Figure 2:
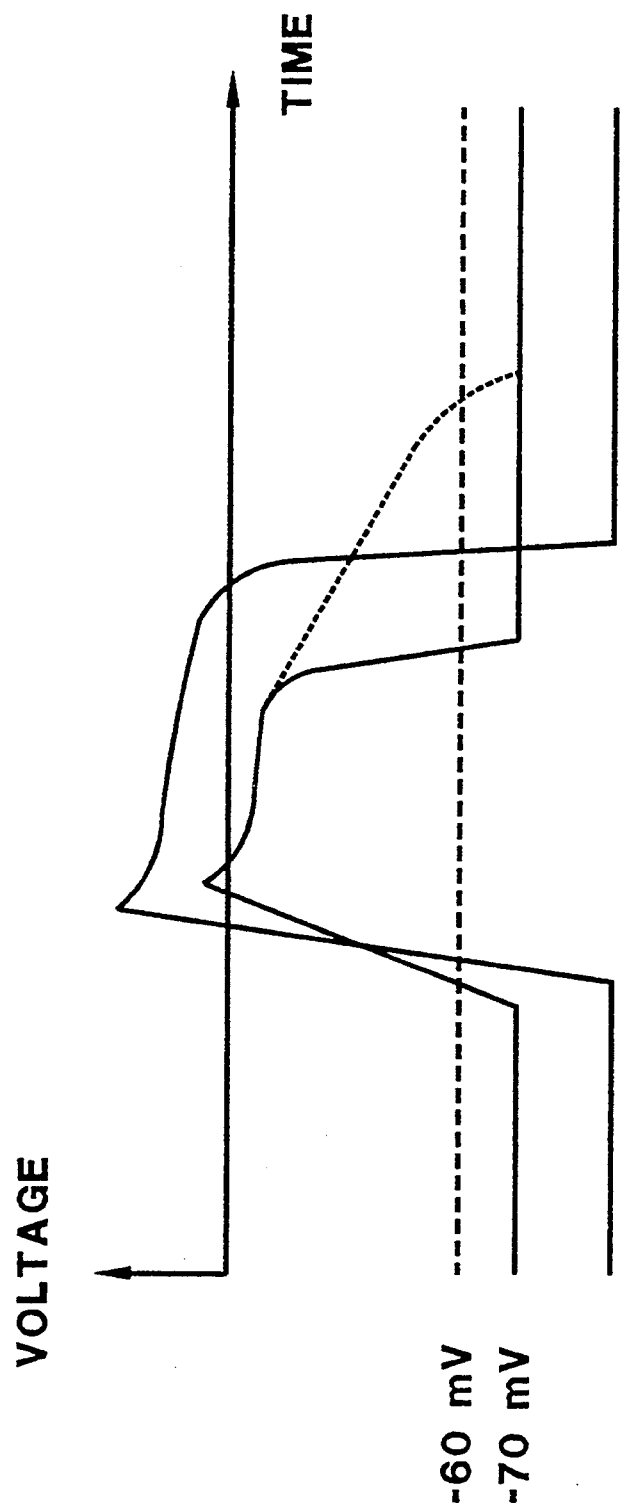
FIG. 2 shows the transmembrane action potentials of two "unstable" cells superimposed on that of a normal cell.

FIG. 2 shows the action potential of two abnormal cells superimposed on a normal action potential. Note that the resting potential is much less negative, the onset slew rate is diminished, and the plateau voltages are reduced. The potential duration is reduced in one cell but is increased in the other. Both can occur.

Figure 3:
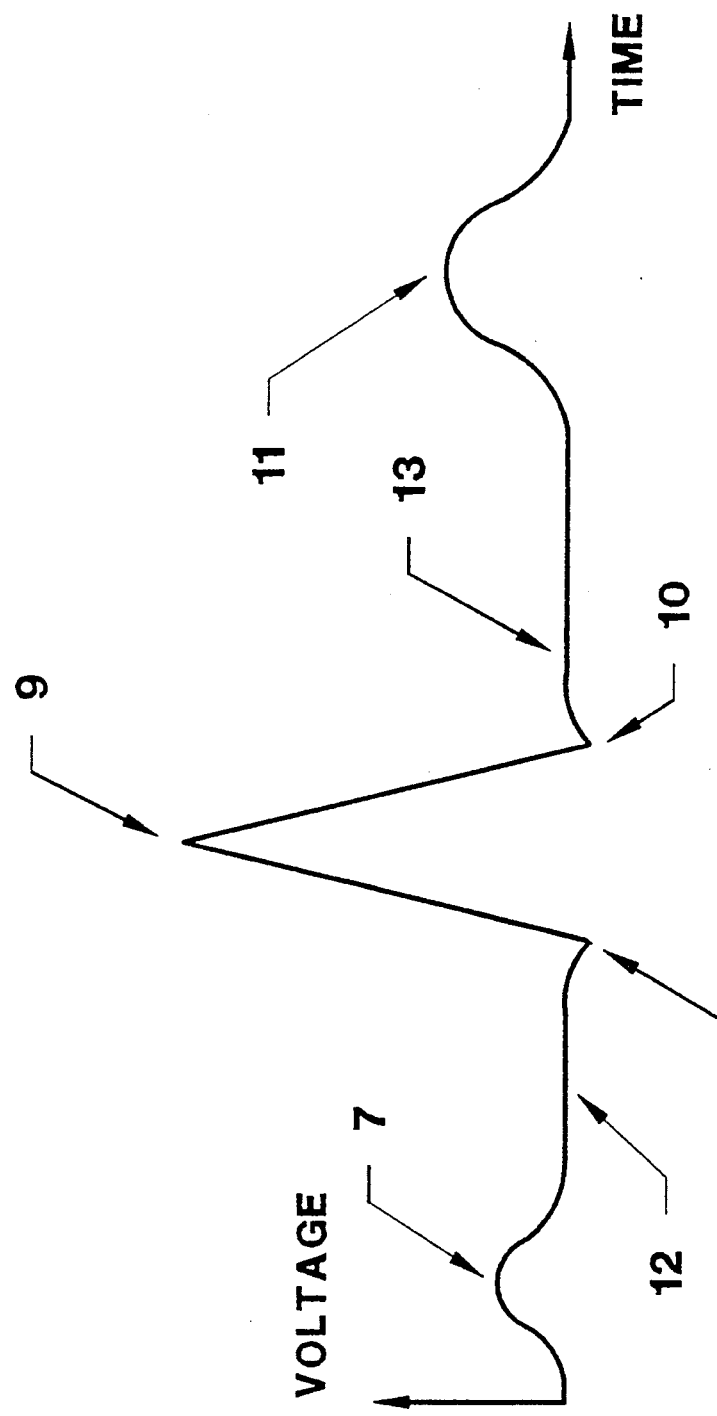
FIG. 3 is a normal skin surface EKG.

FIG. 3 shows the skin surface electrocardiogram (EKG) of an adult human. The first rounded deflection 7 is the P wave and represents the top chambers (atria) of the heart firing to prefill the ventricles for the main pumping action of the heart. The P wave is rather small as there are comparatively few cells firing.

The most pronounced feature of the EKG is the QRS complex. This represents the firing of the ventricles. It is caused by the collective current generated by the cells going through the onset of their action potentials. The first downward deflection is called the Q wave 8. The first upward deflection is the R wave 9. The trailing downward deflection is the S wave 10. When one is merely trying to differentiate between the QRS complex and, say, the P or T waves, the QRS complex is often referred to merely as the "R wave."

The final rounded feature of the EKG is the T wave 11. This represents the repolarization of the ventricular cells and hence the collective currents of the cells going through their repolarization transitions.

The time between the P wave and QRS complex is called the PR interval 12. The voltage line between the QRS complex and the T wave is called the ST segment 13.

Figure 4:
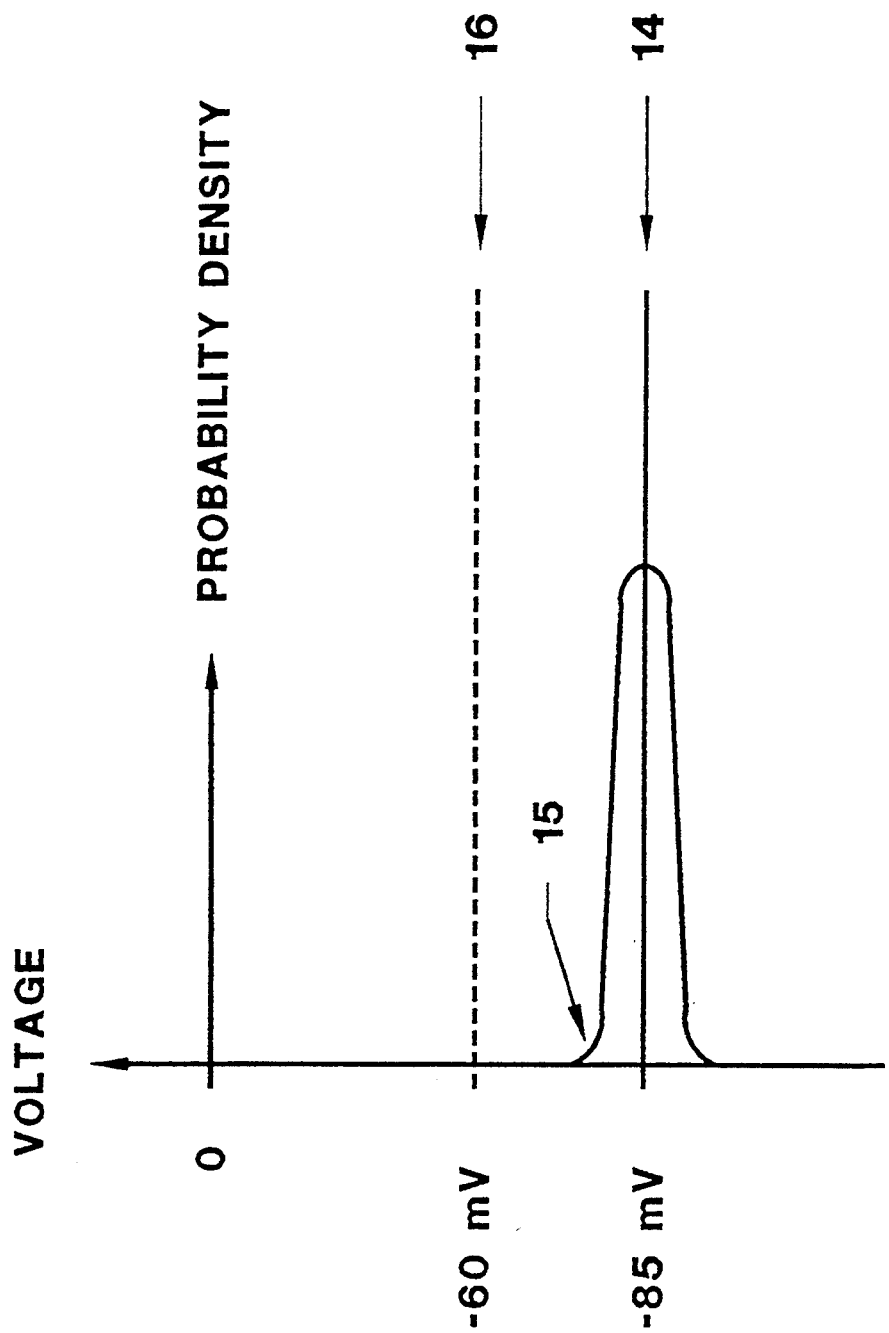
FIG. 4 shows the distribution of resting potentials in a normal heart.

FIG. 4 shows a probability distribution (fine-grained histogram) of the resting potentials of the ventricular cells in a healthy heart, The mean and mode 14 are both at approximately −85 mV. Note that the 99th percentile point 15 is well away from the threshold voltage 16. In other words, the cells in a healthy heart are (electrically) far away from firing.

Figure 5:
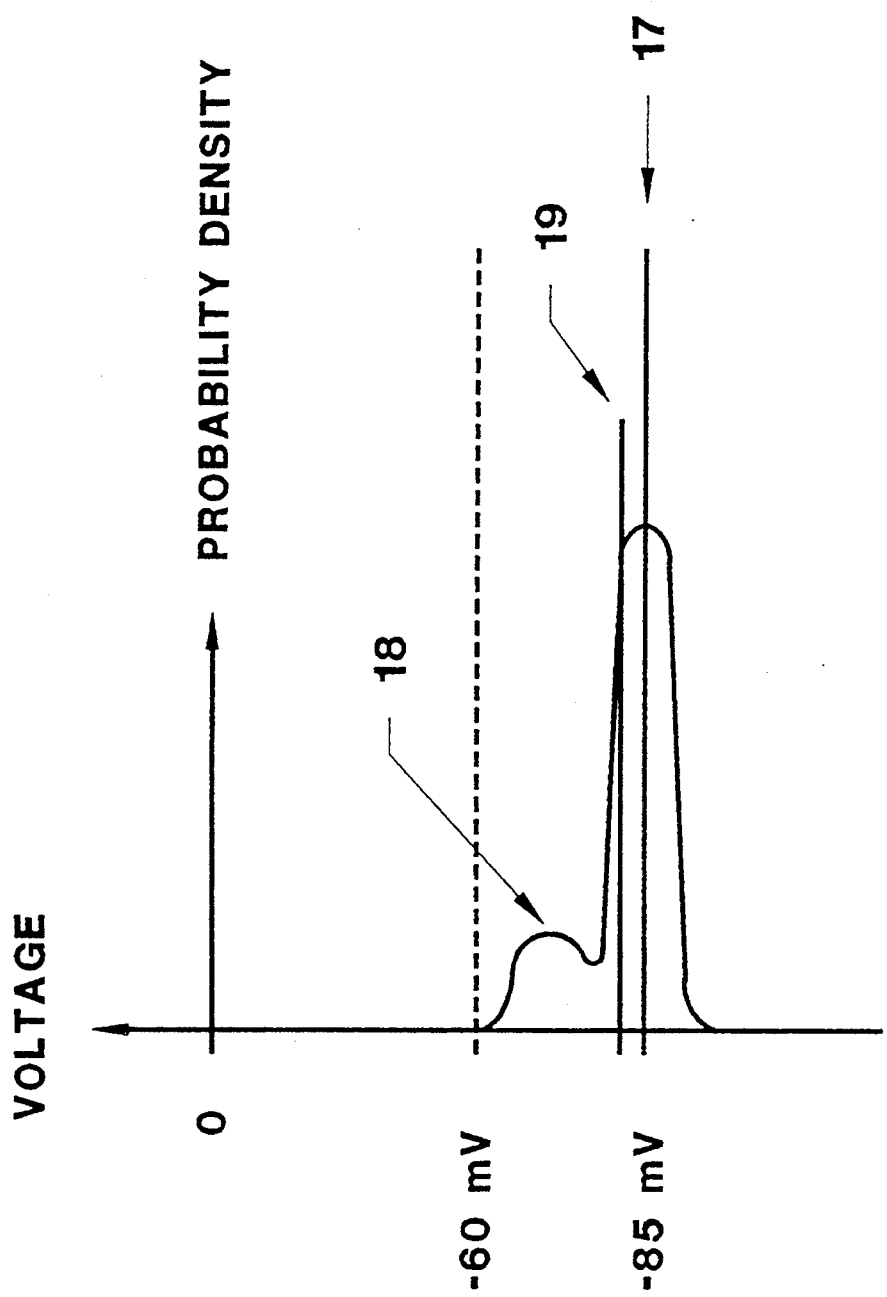
FIG. 5 shows the distribution of resting potentials in a heart with some unstable cells.

FIG. 5 shows the probability distribution of the resting potentials of the ventricular cells in a diseased heart. Note that the mode 17 is still at approximately −85 mV. Because some of the ventricular cells have less negative (or "decreased") resting potentials, the overall distribution is no longer symmetrical and Gaussian. It is now skewed and may even be bimodal with a more positive secondary mode 18. The median resting potential 19 is now slightly more positive. Of critical importance is the fact that the 99th percentile is now much closer to the threshold voltage.

Figure 6:
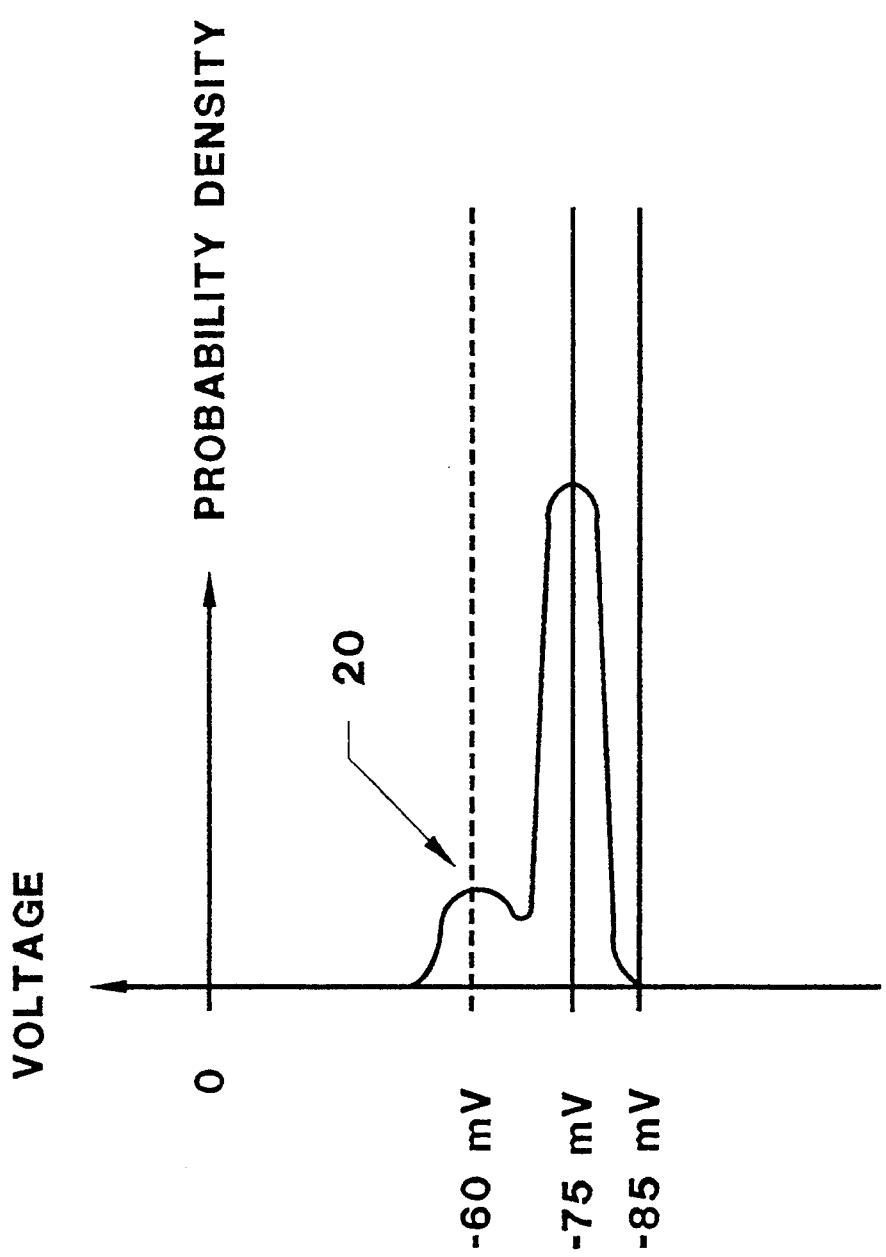
FIG. 6 shows the effect of a small biasing current on the resting potential distribution.

FIG. 6 shows the possible effect of a biasing current through the heart. A current, in the right direction, may decrease (make less polarized, i.e. more positive) the resting potential of a cell. With the appropriate current through the heart, there will be a voltage gradient and the probability distribution of the resting potentials will be shifted up. Here the median resting potential is no longer −85 mV. Those cells, 20 in a diseased heart, whose resting potentials were already close to the threshold voltage, may now be shifted over the threshold. These cells would, of course, fire immediately and thus this section of the probability distribution represents a very transient situation.

Figure 7:
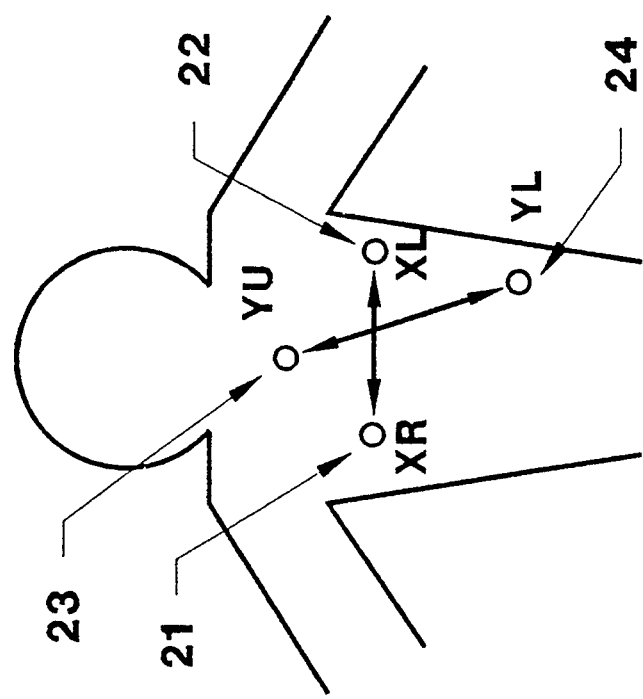
FIG. 7 shows the electrode connections on the front of the human body.

FIG. 7 shows the electrode positions for introducing the low biasing current into the patient's chest. Electrodes XR 21 and XL 22 are used to drive a horizontal or "transverse" current across the chest. They are alternately given the positive polarity (left to right or right to left) to maximize the total number of cells that experience biasing. Electrodes YU 23 and YL 24 are used to drive a largely vertical current through the chest. Again, their polarities are alternated. Sensing electrodes are in the traditional (12-lead) positions or in additional physician selected positions and are not shown here.

Figure 8:
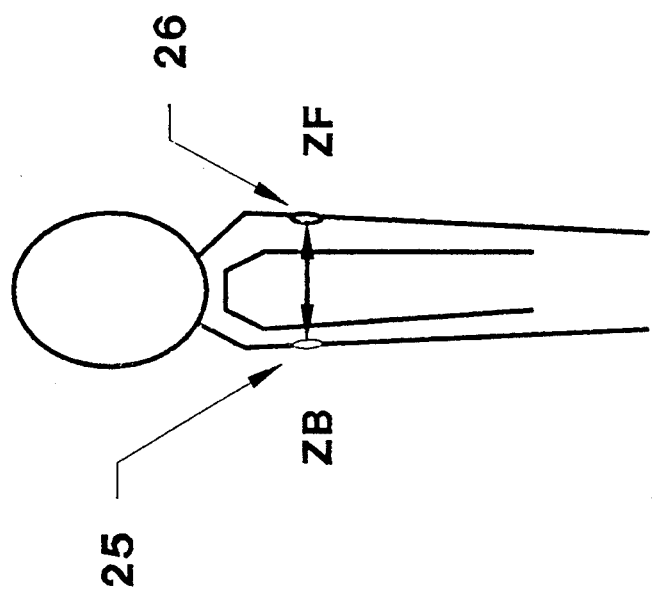
FIG. 8 shows the electrode connections on the the human body for the Z-axis current (front to back).

FIG. 8 shows the electrode positions for introducing the low biasing current directly through the patient's chest from the front to back and vice-versa. Electrodes ZB 25 and ZF 26 are used to drive this "Z-axis" current through the chest.

Figure 9:
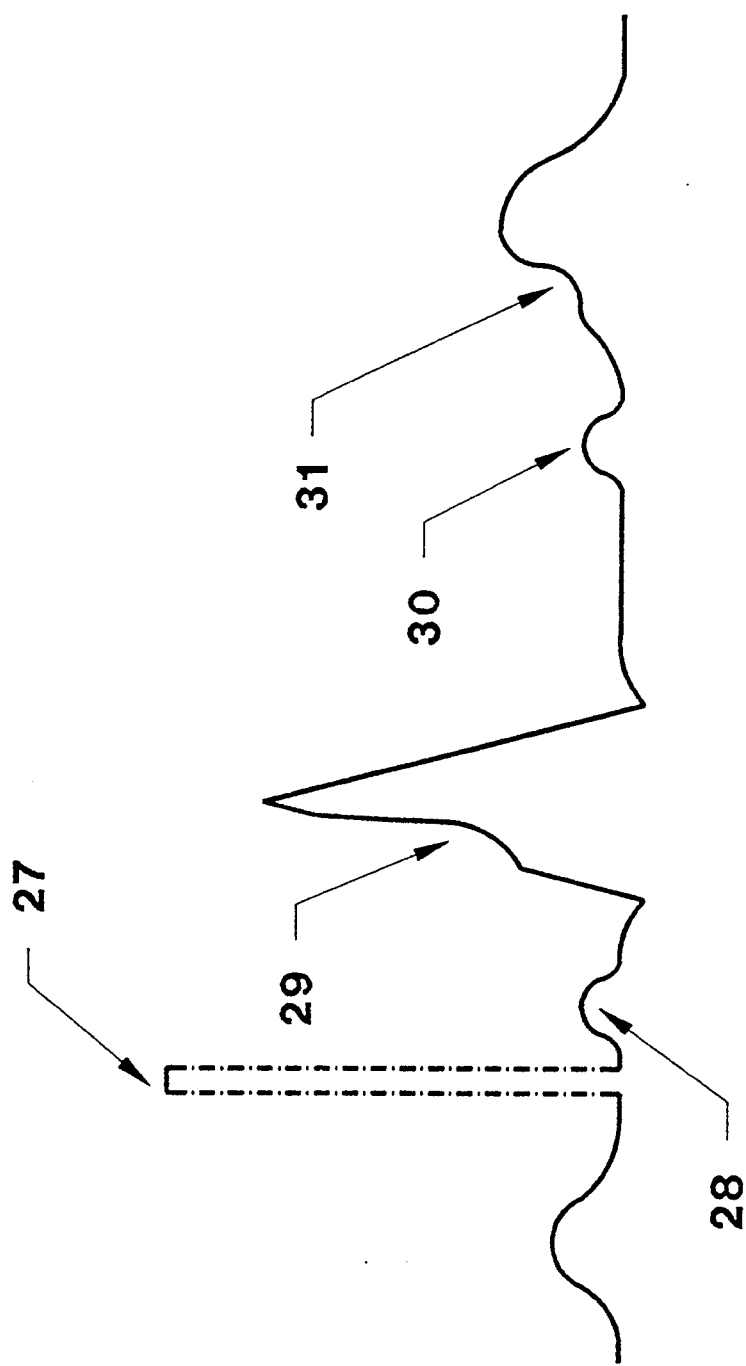
FIG. 9 shows the EKG with the delivery of a current pulse and the effects of the pulse on an unstable heart.

FIG. 9 shows the biasing current pulse 27 in its time position on the EKG with an idealized response of a diseased heart. The changes to the EKG shown here are very exaggerated as the actual effects of the biasing pulse would not typically be visible to the human eye. The first change shown is an immediate response to the biasing pulse. In this case, cells that were near the threshold fired immediately after the pulse producing a small deflection 28. The next change is in the QRS complex 29 and represents the loss of contribution of those earlier firing cells which would have normally contributed to the R wave.

When the pre-stimulated cells repolarize, they again affect the EKG. First, their repolarization occurs earlier than the T wave and thus, can cause a deflection in the ST segment 30. The next change is in the T wave itself 31 and represents the loss of repolarization contribution of those earlier firing cells which would have normally contributed to the T wave.

Figure 10:
FIG. 10 shows the voltage difference between the pulsed and control (unpulsed) EKG.

FIG. 10 shows the algebraic difference between the conventional (passive) EKG of FIG. 3 and the biased EKG of FIG. 9. One of these difference waveforms is calculated, displayed, and printed for each combination of sensing electrode, current, pulse duration, biasing orientation (horizontal or vertical), and biasing polarity (top or left or back electrode positive vs. bottom or right or left electrode positive). This waveform is averaged for many cycles and the integrated absolute voltage difference of the averages is reported as a measure of cardiac instability. This value is called the "early potential measure" and is given by:

$$EPM = \int_P^P \left( \left| \sum_{j=0}^{15} E_{4j+1}(t) - E_{4j+2}(t) \right| + \left| \sum_{j=0}^{15} E_{4j+2}(t) - E_{4j+3}(t) \right| \right) dt$$

Equation 1.

where the integral is given over the cardiac cycle from one P wave to the next with blanking during the actual stimulation pulse time. "E" is the EKG voltage with respect to time. The modulo 4 summation indices refer to the fact that the stimulation changes every 4 cardiac cycles from positive, zero, negative, and finally back to zero. The choice of 16 cycles for averaging is somewhat arbitrary. The operator can choose any number and thus select a reasonable compromise between patient convenience and noise rejection.

Figure 11:
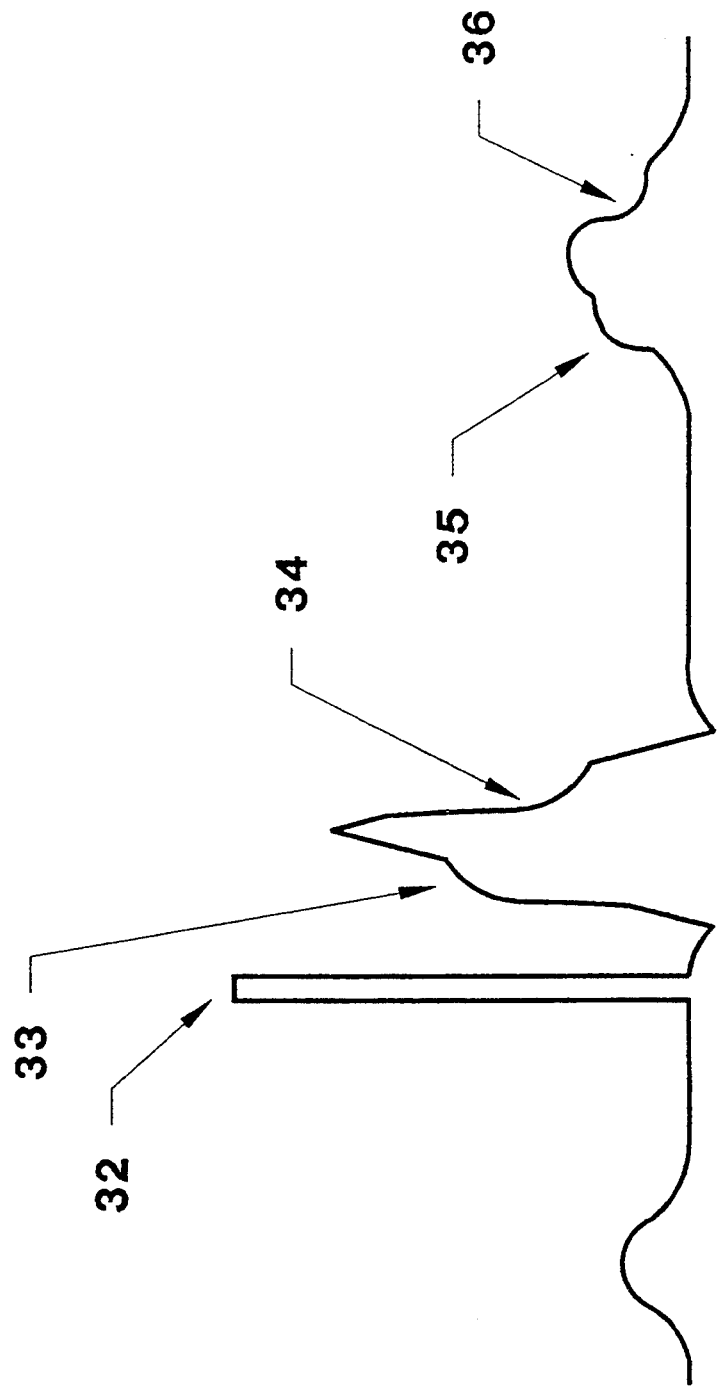
FIG. 11 shows the pulsed EKG for a Wedensky facilitation test with a stimulus pulse located at the QRS onset.

FIG. 11 shows the possible effect of a biasing current pulse at the QRS onset 32. All of the changes shown in FIG. 9 are still possible but are left off of this figure for clarity. Another effect is emphasized here which is slightly different in principal from the directly stimulated early potentials. The stimulation of the biasing current pulse may not have been strong enough, on its own, to have caused the unstable cells to fire as was shown in FIG. 9. However, the earlier partial ("subthreshold") stimulation may increase the sensitivity of a cell so that it fires earlier in the cardiac cycle than it normally would. An increase in sensitivity of a neurological cell due to a shortly earlier subthreshold stimulation is called a Wedensky facilitation.

The Wedensky facilitation may cause an unstable cell that was normally triggered by the electrical wave going through the heart to fire while the wave is some distance away because of the increased sensitivity. If there were any unstable cells, this would cause a shift of some of the energy of the QRS complex towards the first stages. This would cause a distortion in the early part of the QRS 33 with a compensatory and opposite distortion in a later region 34.

A similar effect can occur in the T wave. This figure also shows a distortion in the early part of the T wave 35 with a compensatory and opposite distortion in a later region 36.

Figure 12:
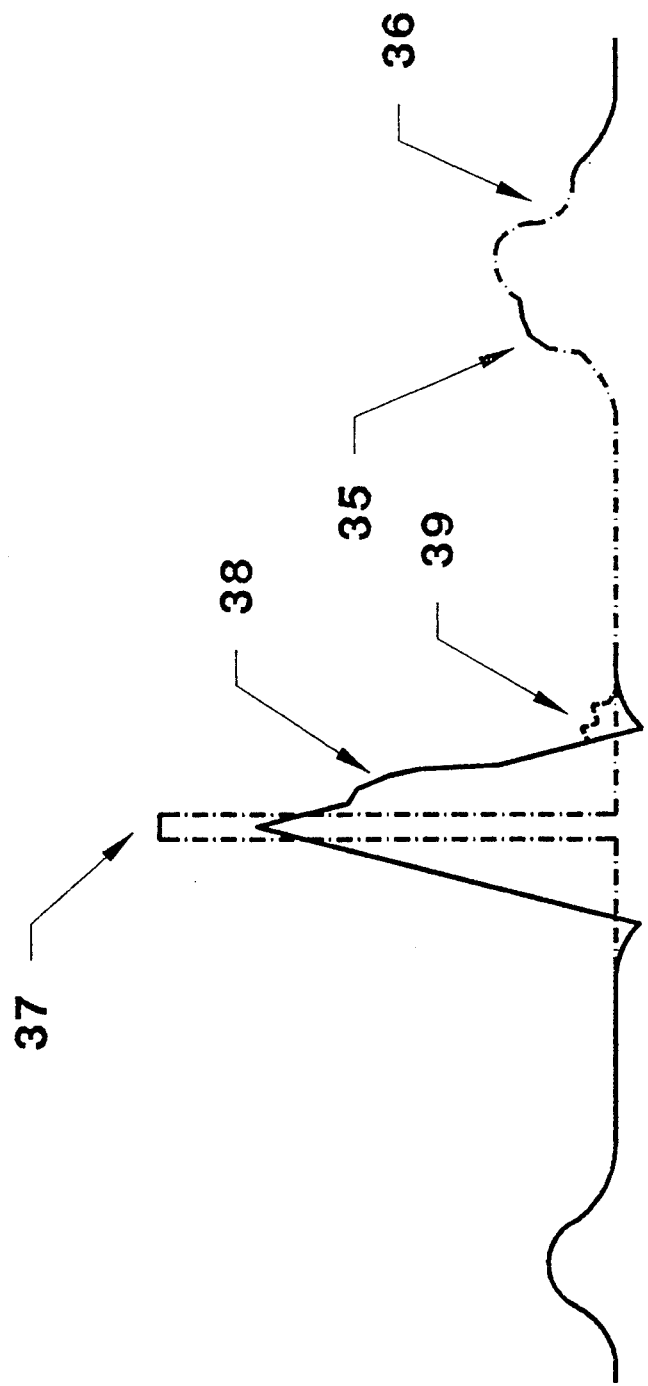
FIG. 12 shows the pulsed EKG for a Wedensky facilitation test with a mid QRS pulse location.

Refer now to FIG. 12. The Wedensky facilitation lasts for about 50 mSec after the subthreshold stimulating pulse. Thus to cover the QRS complex (which is nearly 100 mSec wide) one needs to stimulate again in the center of the R wave 37. Also shown is a distortion in the late part of the QRS 38 from cells that are now able to fire earlier. The dotted signal in the S wave area represents abnormal cells that had such a slow response that their firing did not usually occur until after the main R wave activation 39. These "late potentials" are often seen with averaging in conventional passive EKGs. With the Wedensky facilitation from the biasing current pulse these cells will tend to fire during their appropriate time and thus there will be a decrease in the late potential region. This activity will tend to shift ahead into a part of the QRS more closely following the stimulus pulse.

As mentioned in the Summary, slow conduction can be a cause of ventricular arrhythmias. With the use of a Wedensky facilitation stimulation, the slower responding cells can be detected. The difference waveforms and integrated voltage difference measure are calculated just as they are for the early potentials as shown in Eq. 1.

Thus the bias pulsed waveform (e.g. FIG. 9) and the difference waveform (e.g. FIG. 10) can be fairly complicated. However, the integrated voltage calculation of the difference waveform will include the contributions of the various shifts and hence give a measure of the total level of cardiac instability for both the early potential test and the early (QRS onset) and mid QRS stimulation test.

Figure 13:
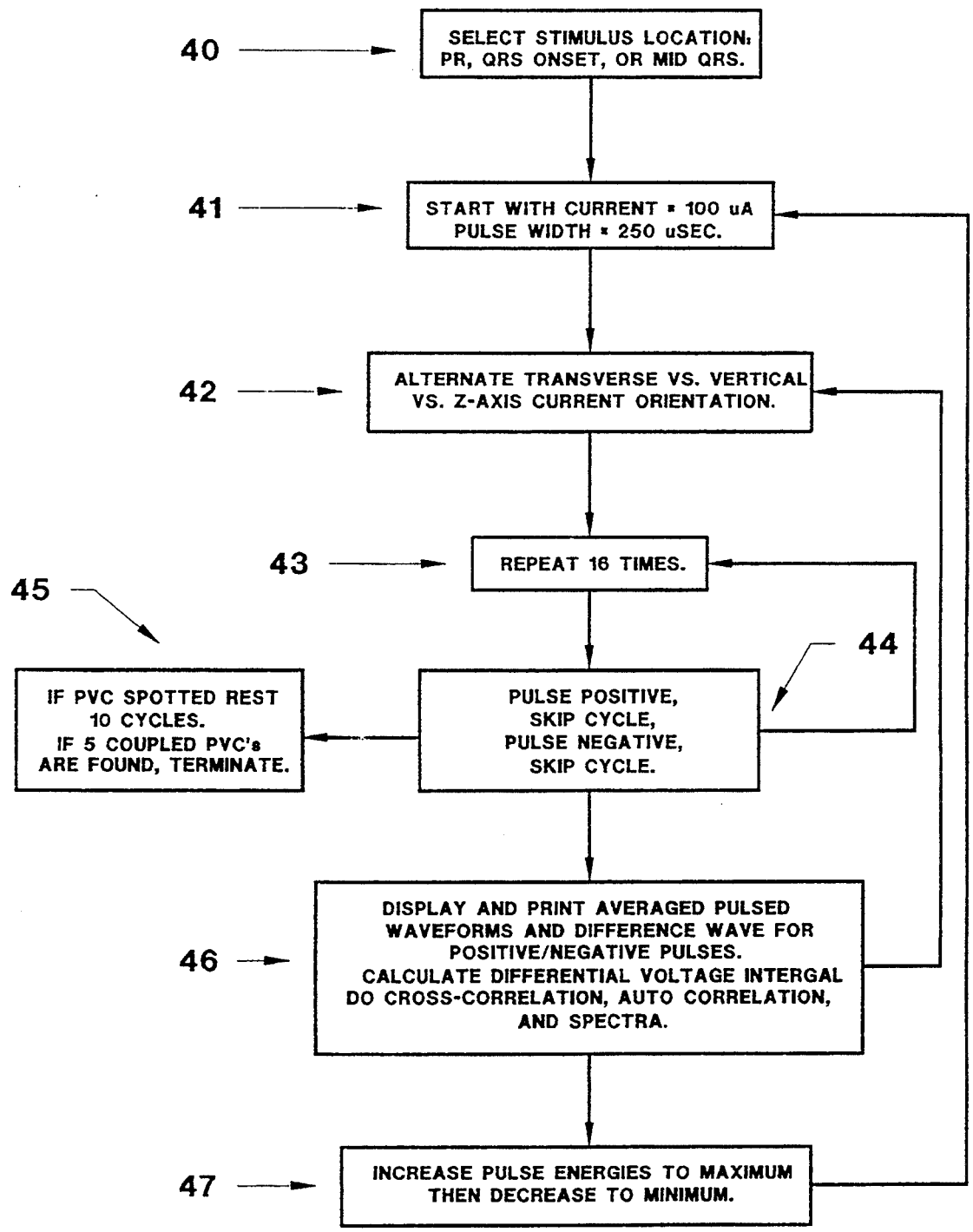
FIG. 13 is a flowchart listing detailed steps of the method.

FIG. 13 is a flow chart of the method. The operator selects a stimulus temporal location of PR interval, QRS onset, mid-QRS, or even the ST-segment or T wave 40. The test begins with a minimal energy biasing current pulse of approximately 100 μA and a width of approximately 250 μsec 41. The orientation is first set at vertical which means that the current flows through the electrodes YU and YL. The orientation is then alternated to transverse for the next pass through the procedure 42. Finally, if the operator desires, a Z-axis pass is made.

For each orientation and biasing current pulse energy level, the biasing cycle is repeated approximately 16 times to allow for signal averaging for noise reduction 43.

The basic innermost cycle involves a positive biasing current pulse, a zero bias cycle, a negative bias cycle, and a zero bias cycle 44. If a PVC is caused by the biasing, the system automatically "rests" for 10 cardiac cycles for safety 45. If, however, a total of 5 PVCs are generated then the test is terminated.

For each combination of sensing electrode, current, pulse duration, biasing orientation (transverse, vertical, or Z-axis), and biasing polarity (top or left or back electrode positive vs. bottom or right or front electrode positive) the resulting (averaged) waveform and difference waveform are displayed and printed 46. The integrated voltage of the absolute value of the average difference is reported as a measure of cardiac instability by Eq. 1.

A cross-correlation is calculated between the stimulus and the difference waveform. As is well known in the art of signal processing, the peaks of the cross-correlation function then show how much delay exists between the stimulus and the response. This gives an estimate of the response speed of the abnormal cells which is valuable for the classification of the abnormal cells.

An auto-correlation is calculated of the response (with itself). As is well known in the art of signal processing, auto-correlation finds time delays between similar portions of the same signal. This will estimate the time between the depolarization and repolarization of the abnormal cells. This time is the potential duration and is valuable for classifying these abnormal cells.

A frequency spectrum is calculated of both the averaged QRS complex and the averaged difference waveform responses. The median frequency is calculated for each. The ratio of the median frequencies is calculated. As is well known in the art of electrical engineering, the slew rate of a pulse edge is directly proportional to its frequency content. This estimates the relative ratios of the slopes of the firing of the abnormal cells to the normal cells. As slow responding cells are especially capable of causing ventricular arrhythmias this information is valuable for the diagnosing physician.

The pulse energy is then increased one step and the process is continued until the safety maximum is reached 47. At that point, the process may be reversed, at operator option, and the biasing current pulse energy is steadily decreased until the starting minimums are reached. The physician can thus compare ascending values to descending values to check for hysteresis phenomena.

Figure 14:
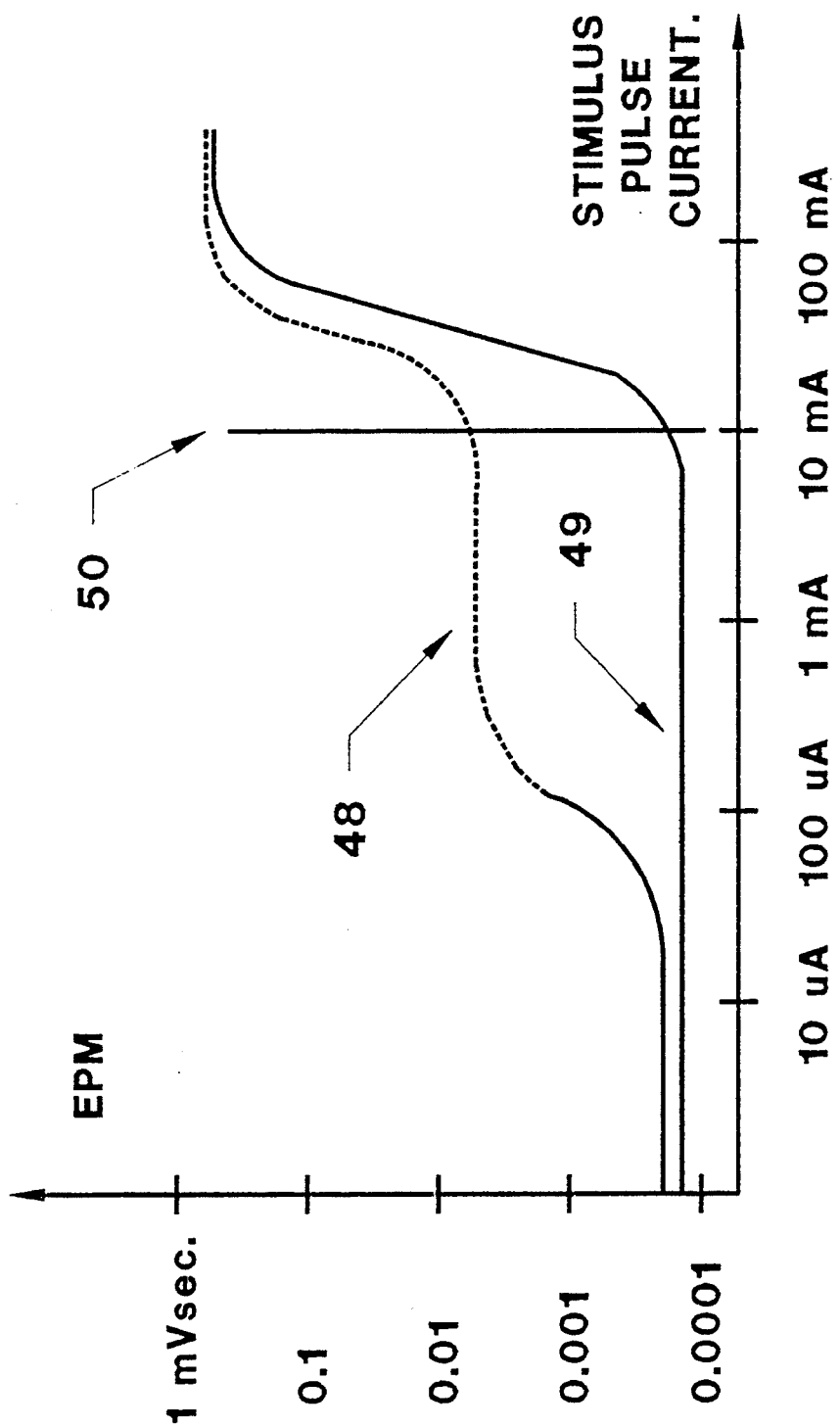
FIG. 14 shows the dose response curves for an inducible and normal patient.

FIG. 14 shows two dose response curves for the early potential measure (EPM) versus the biasing current pulse strength for a fixed width of 10 mSec. The top curve is for an inducible patient 48. Note that the EPM first moves up from the noise floor at a small current while the normal patient's curve remains at the noise floor 49. Of course, if the pulse current were increased substantially beyond the safety limits of 10 mA 50 then pacing would occur and the EPM would grow very large for either patient.

Figure 15:
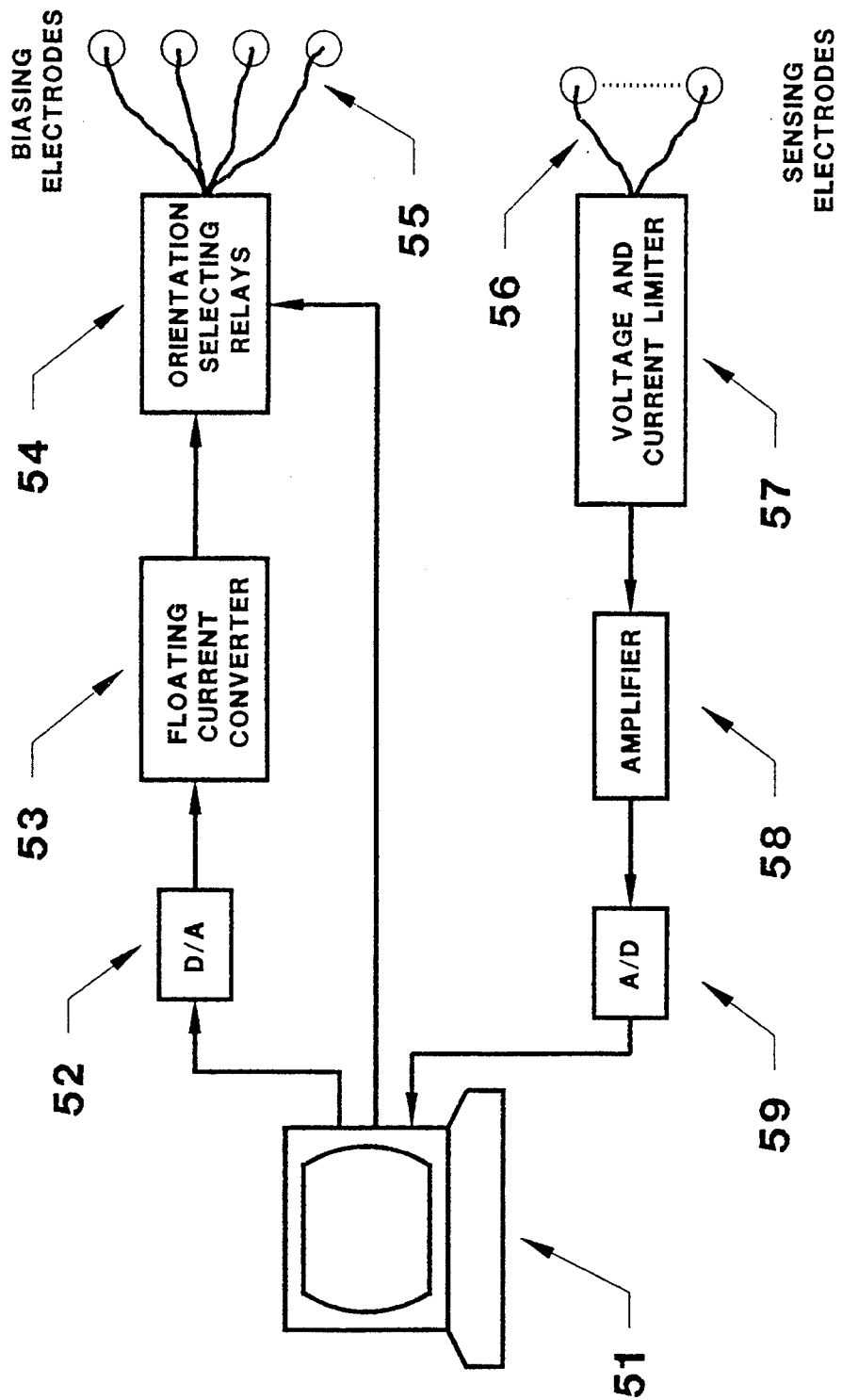
FIG. 15 is a block diagram of the device.

FIG. 15 is a block diagram of the device. A small work station (or high performance personal computer) 51 is connected to a digital to analog converter 52 to generate pulses of the proper timing and voltage. These pulses are then fed into a floating current converter 53 which generates a differential current which is then fed into the orientation selecting relays 54. These relays (also under computer control) select the electrodes 55 to receive the biasing current pulse.

Sensing electrodes 56 deliver the patient's EKG signals to a voltage and current limiter 57. The signals then go through an amplifier, 58 an analog to digital converter, 59 and finally into the work station for analysis.

Figure 16:
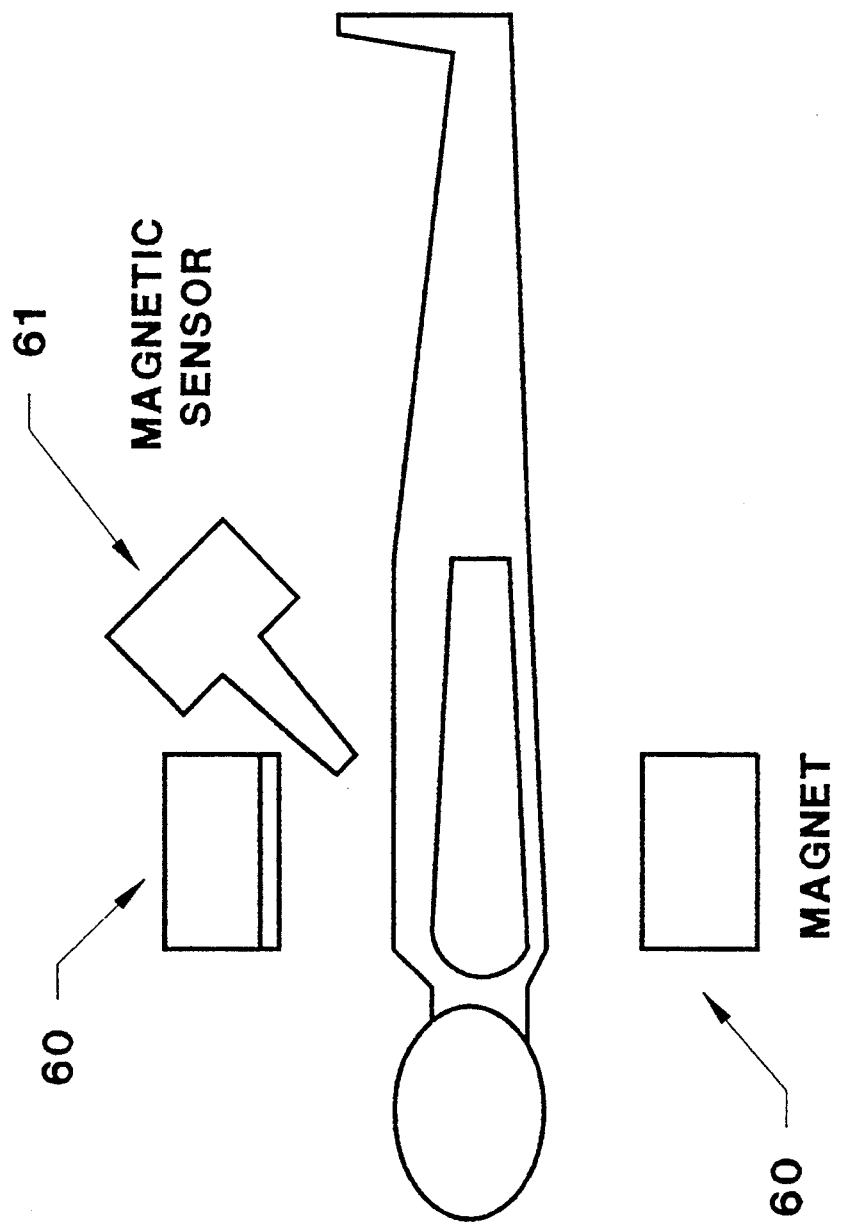
FIG. 16 shows an alternative embodiment of the invention using magnetics.
Figure 16A:
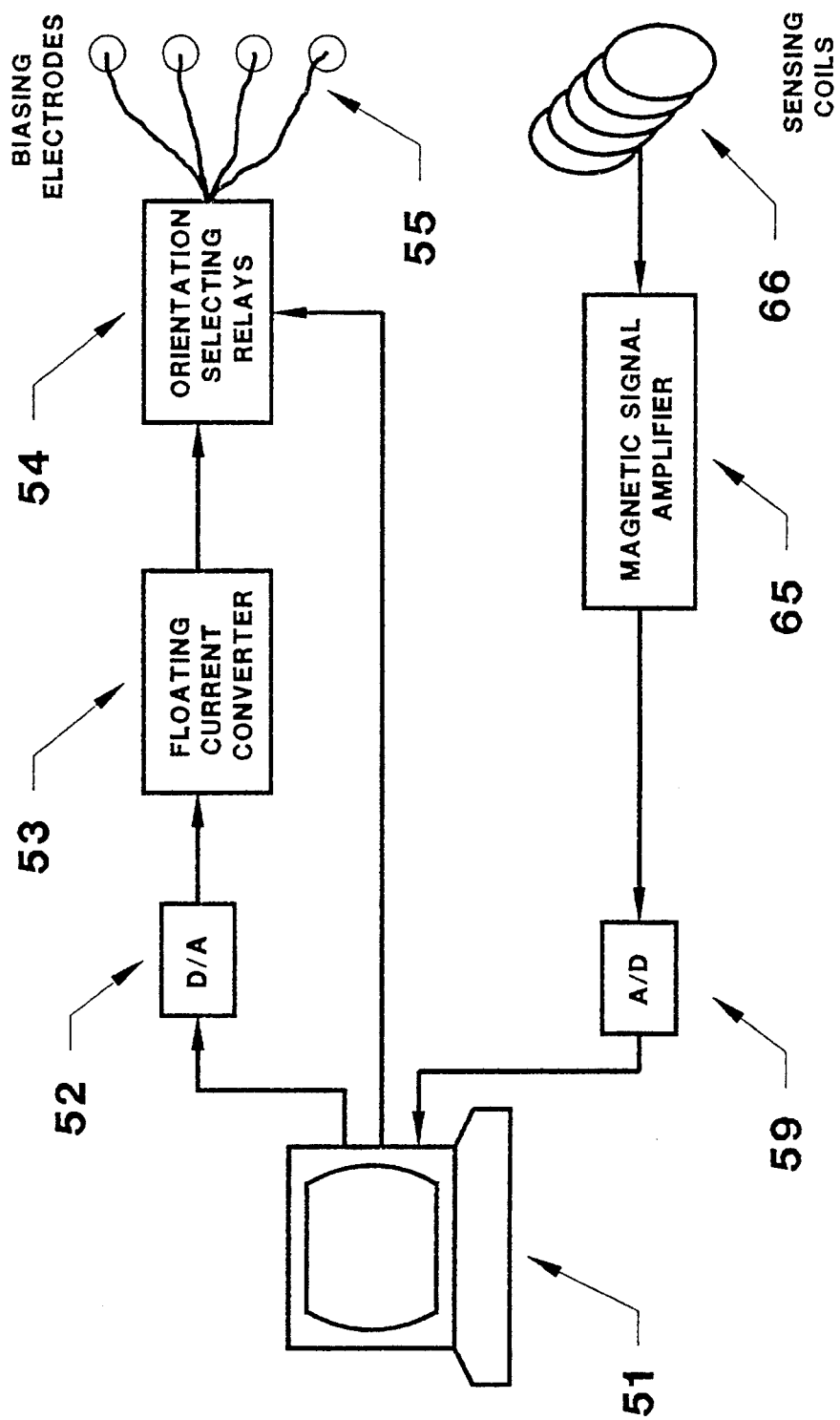
FIG. 16A shows a particular instance of a magnetic embodiment in which electrical stimulation is used with magnetic sensing.

FIG. 16 shows an alternative embodiment of the invention, Here, magnets 60 deliver the stimulating energy and a magnetic sensor 61 detects the response. The advantage of this embodiment is that the patient does not need electrode preparation (such as shaving) and application. A further advantage is that, with multiple magnetic sensors, it is possible to do imaging and thus one could image the response of the unstable cells. A disadvantage is that the magnets and magnetic sensors are expensive. Hybrid approaches are possible. For example, one could use magnetic stimulation and the electrical sensing shown in FIG. 15 and vice versa. The hybrid approach in which electrical stimulation is used with magnetic sensing is shown in FIG. 16A. Magnetic sensin coils 66 pick up the magnetic signal from the heart, typically referred to as the "magnetocardiographic signal", and send them to the magnetic signal amplifier 65. The other items of the system are identical to those shown in FIG. 15. Similarly the stimulating magnets drawn could actually represent large capacitive plates which would stimulate through capacitive (electrostatic) coupling. Sensing would be either magnetic or conductive (through electrodes).

FIG. 17 depicts another alternative embodiment of the invention. Here a burst of higher frequency stimulation 62 is placed in the PR interval. It could just as well be placed in the QRS complex. Through the technique of synchronous demodulation (well known in the art of signal processing) the stimulation signal itself can be removed from the EKG signal. The advantage of this approach is that the response can be seen and voltage difference integrated throughout the cardiac cycle without confusion with the stimulation itself. A disadvantage is that the cardiac cells do not respond strongly to very high frequencies.

Figure 18:
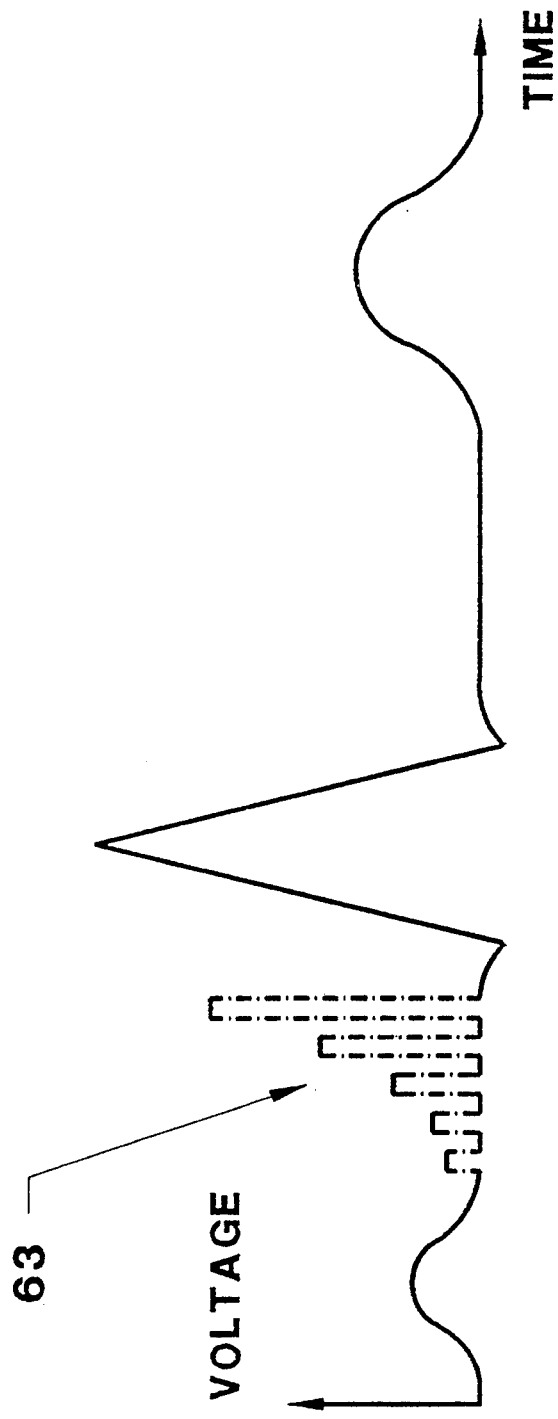
FIG. 18 shows an alternative embodiment of the invention using a crescendo pulse train for stimulation.

FIG. 18 shows another alternative embodiment of the invention. Here a crescendo train of pulses 63 is used for stimulation. A burst of higher frequency such as that shown in FIG. 17 can also be used with crescendo modulation. Synchronous demodulation is again used to separate the stimulus from its result. With the amplitude rising with every individual stimulus pulse, the EKG response is checked in between. If a voltage response over 100 $\mu$V is sensed, then it is suspected of being a PVC and the stimulation level is frozen or the test returns to a normal procedure as shown in FIG. 13. The advantage of this approach is that the test can be run much more rapidly since many increments can be made in one cardiac cycle. The disadvantage is that the responses may not fully develop between pulses and thus the accuracy may suffer.

It is preferred, for safety reasons, that the biasing current pulse occur in the PR interval or QRS complex. With sufficient strength the biasing current pulse could enlist enough cells so that a cascade occurs and the ventricles fire before the normal time. This is called a premature ventricular complex (PVC). The average person may have several PVCs during the day and they are not considered dangerous at that level. If the biasing current pulse were to cause a PVC in the PR interval, the heart would merely contract slightly earlier with slightly less efficiency. There is also no danger in the QRS since the heart is already firing. If, however, PVCs were to occur repeatedly in the middle of the T wave, ventricular tachycardia could occur. Hence it is preferred to deliver the biasing current pulses in the PR interval and QRS complex.

Biasing current pulses could, however, be delivered later in the cardiac cycle to measure such parameters as recovery and refractoriness (receptiveness to another pulse). The system would have to diligently monitor the heart's responses.

As an alternative embodiment, the stimulus pulse could be placed in the middle of the T wave and the response tested. The advantage of this embodiment is that it closely mimics the timing of invasive inducibility studies. A disadvantage is that it has a risk of fibrillation with a sufficiently strong pulse.

As an alternative embodiment, the stimulus pulse could be of a larger strength of approximately 100 mA and 10 mSec wide. An advantage of this embodiment is that it would completely capture the heart (pace) and the changes to the EKG would be much more dramatic. A further advantage is that the pulse (or multiple pulses) could be placed in or after the T wave and thus more closely mimic the approach of invasive inducibility studies. A disadvantage is that it has a risk of fibrillation with a sufficiently strong pulse.

As an alternative embodiment, the stimulus pulse could be very wide, such as approximately 100 mSec in order to completely cover the R wave. An advantage of this embodiment is that it would have a better opportunity of stimulating all ventricular cells. A disadvantage is that it is more difficult to separate the pulse signal from the patient's EKG signal.

As an alternative embodiment, the device could have the capability of delivering regularly spaced high strength pulses to restore the heart to a normal rhythm. This technique is known as "overdrive pacing" and is used to recapture the heart from ventricular tachycardia. An advantage of this embodiment is that it would allow for restoration of normal rhythm in case ventricular tachycardia occurred. A disadvantage is that it requires more electronic hardware and could require more operator training.

As an alternative embodiment, the device could have the capability of varying the location of the stimulus pulse until it found a maximal response. It would then continue to pulse in this timing location. An advantage of this embodiment is that it would allow better signal to noise ratios in the signal. A disadvantage is that it could make patient to patient comparisons more difficult and decrease repeatability.

We claim:

1. A device for determining a patient's susceptibility to ventricular arrhythmias, comprising:
   a) means to inject electromagnetic energy into a patient's body at a current of less than 100 milliamperes;
   b) at least one magnetic sensor to detect the magnetocardiographic signals; and
   c) means connected to the magnetic sensor to record the changes in the patient's magnetocardiographic signals caused by the injection of the electromagnetic energy into the patient's body;

thereby sensing the cardiac instability related to ventricular arrhythmias noninvasively.

2. A method for determining a patient's susceptibility to ventricular arrhythmias, comprising the steps of:
   a) injecting electromagnetic energy into a patient's body at a current of less than 100 milliamperes;
   b) monitoring magnetocardiographic signals from at least one magnetic sensor; and
   c) recording the changes in the patient's magnetocardiographic signals caused by the injection of the electromagnetic energy into the patient's body;

thereby sensing the cardiac instability related to ventricular arrhythmias noninvasively.

* * * * *